United States Patent [19]

Seitel et al.

[11] 4,322,967
[45] Apr. 6, 1982

[54] METHOD AND APPARATUS FOR MEASURING OPTICAL COUPLING COEFFICIENTS

[75] Inventors: Steven C. Seitel; James O. Porteus, both of Ridgecrest; William N. Faith, China Lake, all of Calif.

[73] Assignee: The United States of America as represented by the Secretary of the Navy, Washington, D.C.

[21] Appl. No.: 189,401

[22] Filed: Sep. 19, 1980

[51] Int. Cl.³ .......................................... G01N 25/00
[52] U.S. Cl. .................................... 73/15.6; 356/432
[58] Field of Search ............... 73/15.6, 190 EW, 826, 73/800; 356/432; 250/341

[56] References Cited

U.S. PATENT DOCUMENTS 3,645,634 2/1972 Bucher ............................... 356/201
3,902,809 9/1975 Sparks ................................. 356/85
4,041,313 9/1977 Potter et al. ........................ 250/341
4,185,497 1/1980 Decker et al. ................ 73/190 EW

OTHER PUBLICATIONS

National Bureau of Standards, Special Publication 509, 1977, pp. 204–214, "Pulsed-Laser Stress Phenomena on Highly Reflecting Metal & Alloy Surfaces", Purteus et al.

Primary Examiner—Anthony V. Ciarlante
Attorney, Agent, or Firm—Robert F. Beers; W. Thom Skeer; Kenneth G. Pritchard

[57] ABSTRACT

An apparatus and method for measuring optical coupling coefficients is disclosed using the thermal expansion of a sample to reduce an externally applied tensile load of predetermined magnitude. The sample is illuminated with a known amount of incident energy. The absorption of this energy expands the sample which reduces the tension in the sample. The measurement of the tension reduction permits a direct calculation of the coupling coefficient $\alpha$, through use of the known parameters of a sample.

8 Claims, 6 Drawing Figures

METHOD AND APPARATUS FOR MEASURING OPTICAL COUPLING COEFFICIENTS

BACKGROUND OF THE INVENTION

1. Field of the Invention

The present invention pertains to optical testing devices and in particular to optical testing devices for measuring the optical coupling coefficients of materials. In even greater particularity, the present invention pertains to the measurement of optical coupling coefficients through the thermal expansion of material while under a stress load that is monitored.

2. Description of the Prior Art

When optical radiation falls on a substance, energy is absorbed. The ratio of absorbed to incident flux is the optical absorptance. Absorptance depends upon the properties of the optical radiation, such as wavelength, intensity, duration, etc. as well as those of the absorber, such as reflectance, etc. When the intensity is sufficient to alter absorptance, the term coupling coefficient is used to express the fractional energy absorbed in a given time interval. The absorbed energy is converted to heat within the absorbing sample. Coupling coefficients are frequently measured by observing the resultant temperature rise, often by direct instrumentation of the absorber. In general, the prior methods of measuring coupling coefficients are referred to as calorimetric techniques.

Accurate measurement of optical coupling coefficients becomes urgent as the use of high-power laser systems becomes widespread. Ever more frequently, new optical and structural materials undergo intense irradiation at a variety of wavelengths. Problems due to laser-induced fatigue or failure can be avoided or minimized in system design if material response to optical radiation is known.

The hereafter described method and apparatus is a fundamentally different concept for measuring coupling coefficients. The basis is the thermo-mechanical expansion or contraction of the absorber. This provides a direct measure of the total energy absorbed, without considering the temperature distribution in the absorber itself.

SUMMARY OF THE INVENTION

A sample to be tested is placed under a predetermined tension which does not overstress the sample. A load cell or similar device is used to monitor specific tension experienced by the sample. A light source such as a pulsed laser is used to illuminate the sample with light of a known intensity and wavelength. After illumination, a characteristic time is permitted to pass which represents reasonable time for the sample to absorb the energy and let the absorbed heat spread throughout the sample. Thus, peak sample thermal expansion is expected to occur upon passage of the time required to diffuse heat across the sample. The corresponding reduction in sample tension is monitored by a measuring device such as a load cell and recorded. The actual physical measurement of reduced sample tension coupled with known parameters, such as specific heat, mass density, and Youngs modulus and thermal expansion coefficient permit a direct calculation of coupling coefficient $\alpha$ to be made.

DESCRIPTION OF THE PREFERRED EMBODIMENT

Figure 1:
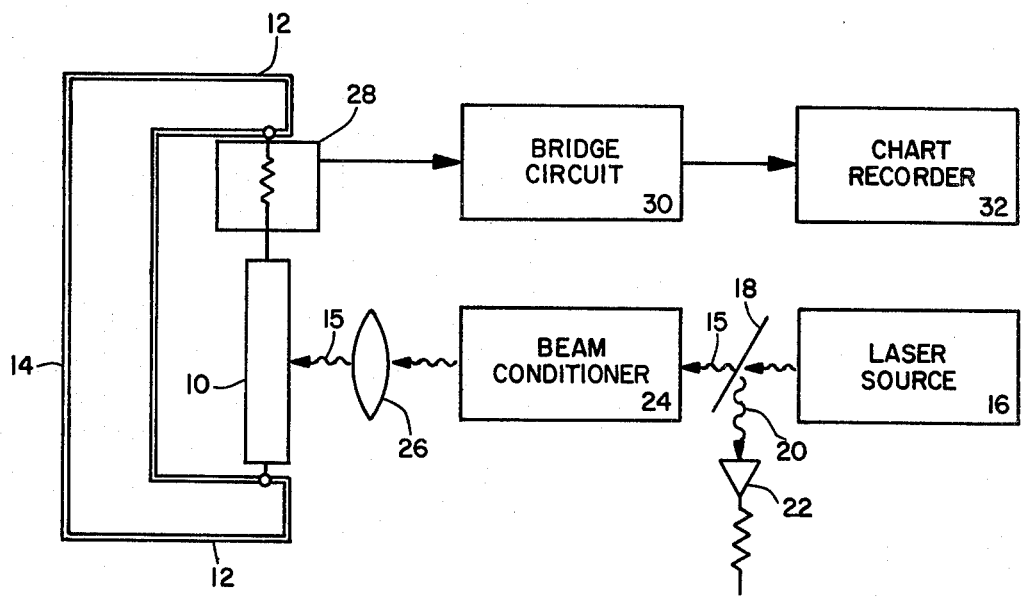
FIG. 1 is a block diagram of a coupling coefficient apparatus and method.

FIG. 1 shows a sample 10, which will be absorbing optical energy, clamped between the jaws 12 of a tensioning device 14. Tensioning device 14 puts a static tensile load within the elastic limit on sample 10 by increasing the separation of jaws 12. Optical radiation 15 is obtained from a light source 16 which can be a pulsed laser source. The light incident on sample 10 is first passed through a beamsplitter 18 which divides the light into two separate pulses 15 and 20 of known relative energy. For example, beamsplitter 18 could be a 50% beamsplitter which would make pulses 15 and 20 of equal energy. Pulse 20 is incident on a reference detector 22 which is a means for detecting the absolute energy of pulse 20. If the absolute energy of one of the pulses from beamsplitter 18 is known as well as the relative energy between the two pulses, the absolute energy of the other pulse may be calculated. By this method, the absolute energy incident on sample 10 from beam 15 is determined. Additional optics, such as a beam conditioner 24 may be used to match the spatial distribution of beam 15 to the geometry of sample 10. A lens 26 can also be used to focus beam 15 onto sample 10. That portion of the incident laser pulse which is absorbed by sample 10 is converted into heat. This heat causes the sample to expand thermally. The expansion is taken up internally by a load cell 28. Load cell 28 is connected to a bridge circuit 30 which measures the change in tension on sample 10. Bridge circuit 30 is in turn connected to a chart recorder 32 or other recording means for displaying the resultant tensile relaxation.

Figure 2:
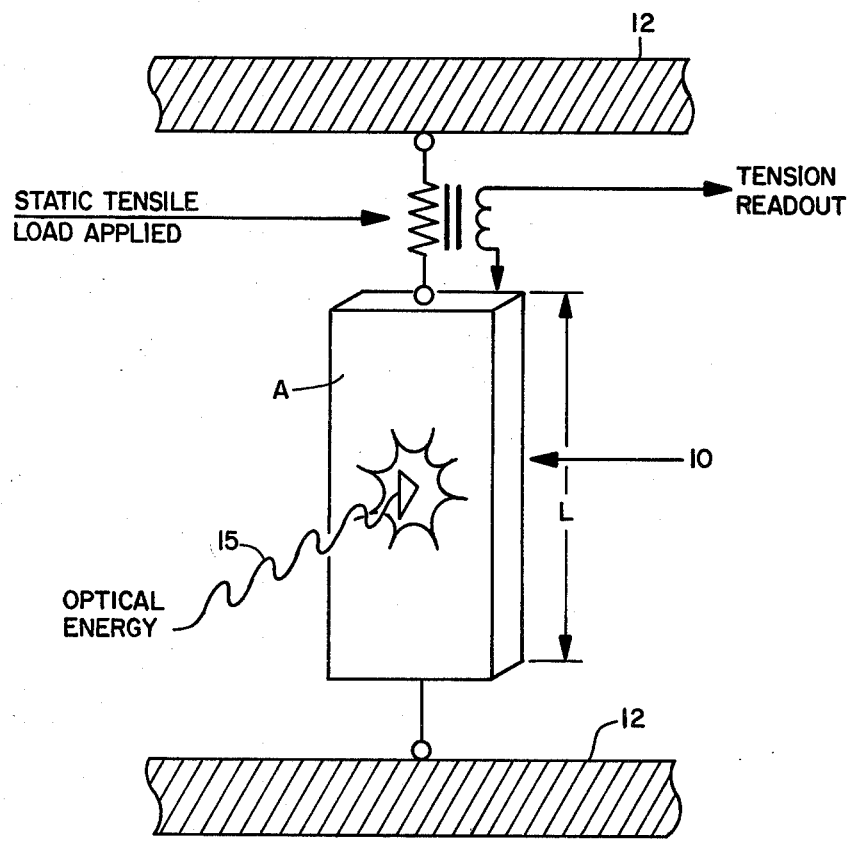
FIG. 2 is a face-on view of an illuminated sample similar to that used in FIG. 1.

A front view of sample 10 is shown in FIG. 2. In FIG. 2, sample 10 has constant cross-sectional area A and length L. Values for the specific heat C, mass density, $\rho$, and linear thermal expansion coefficients, r, are taken from standard tables of physical data and are assumed constant. Young's modulus, Y, can either be taken from tables or measured directly for each sample. The load cell compliance dL/dF also is measured.

The instantanous relaxation depends on the temperature rise, integrated over the sample. Recovery to ambient temperature and tension is governed by the rate at which absorbed laser energy is removed. The dominant mechanism is heat conduction to the massive jaws 12 of tensioning device 14. For a typical aluminum sample of 1 millimeter width, w, and 50 millimeters length L, and 15 millimeters thickness, d. The characteristic time for heat conduction to jaws 12 is approximately one second. This is long compared to a laser pulse duration, 100 nanoseconds, and to the time required to diffuse heat across the sample, 1 millisecond. The peak sample relaxation is an accurate measure of the total laser energy absorbed. The ratio of absorbed to intercepted incident energy is the coupling coefficient $\alpha$. This method has been tested on both painted and unpainted surfaces. Coupling coefficients measured by this method for unpainted samples of bare aluminum are in good agreement with calorimetric values previously reported.

Figure 3:
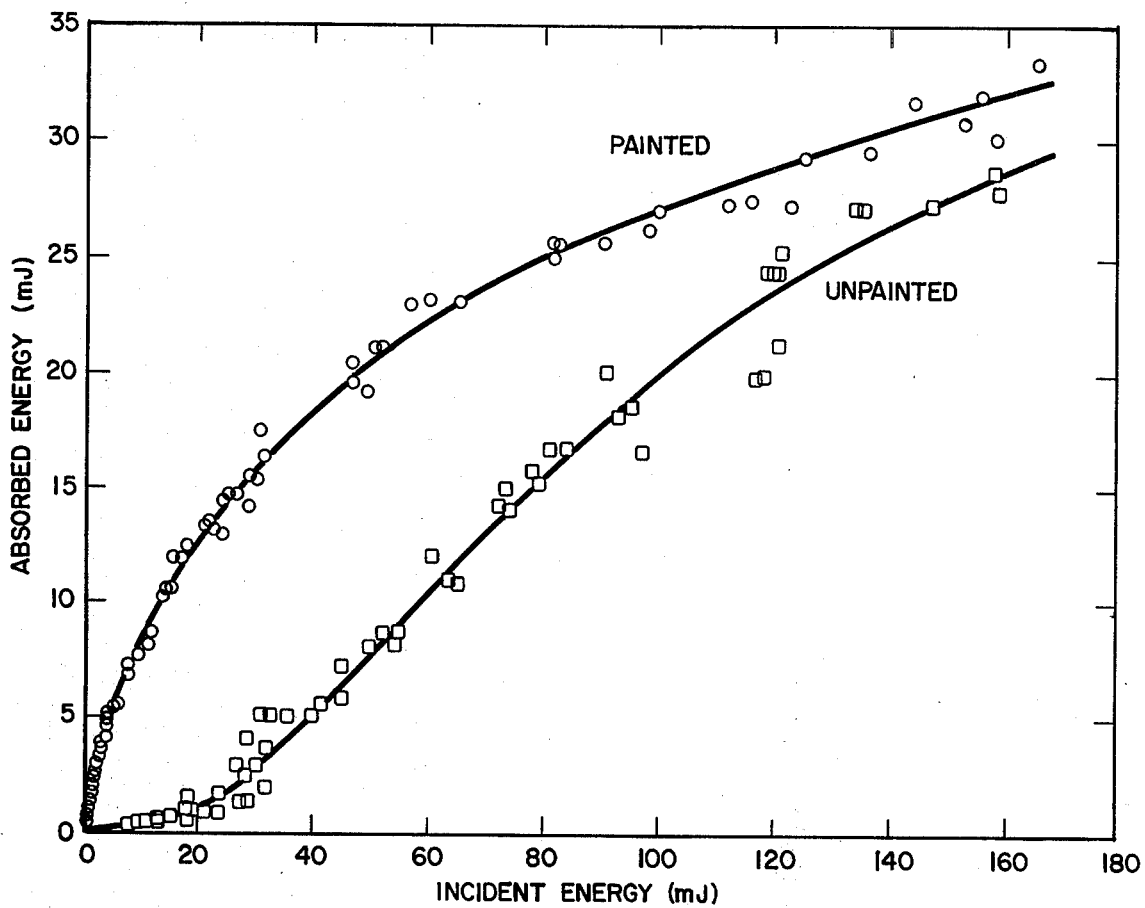
FIG. 3 contains graphs of optical coupling coefficients for two different types of samples.

FIG. 3 shows the energy absorbed by painted and unpainted samples of aluminum as a function of incident energy. The slope is the coupling coefficient $\alpha$. For the unpainted sample, the slope increases dramatically, from 3% to 25%, at an incident energy of approximately 17 millijoules. This energy is also the threshold for initiation of a plasma consisting of ionized gasses formed by evaporation from the surface of the sample during irradiation.

Figure 4:
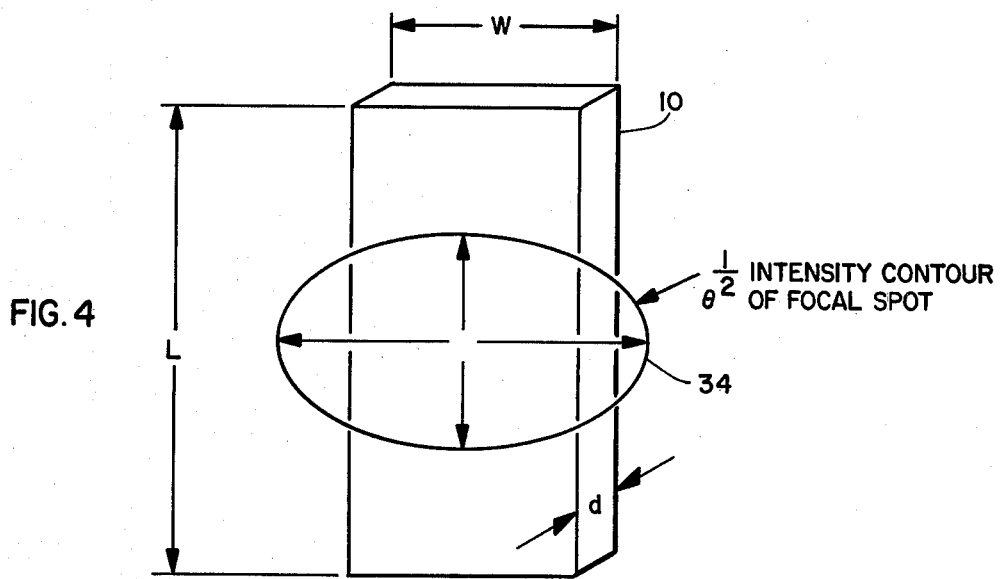
FIG. 4 shows sample illumination.

Coupling above threshold is dominated by the laser-induced plasma, since the plasma produced by the first part of the arriving laser pulse absorbs the remainder of the pulse more strongly than does the reflective bare metal. For pulse energies not far above threshold, thermal contact is maintained between plasma and sample, and more net energy is coupled into the sample than would be the case were the plasma not present. This accounts for the abrupt increase in slope. The plasma expands slowly during the laser pulse and thus enlarges the area over which energy is coupled into the sample. Such "plasma shielding" can explain the observation that massive damage does not occur with unpainted samples in spite of the large amount of energy absorbed. At very large incident energies, the slope $\alpha$ decreases. This is consistent with more rapid plasma expansion, or even detachment, which results in reduced coupling for the sample. Plasma shielding should be less effective with larger irradiated areas on larger targets, since plasma expansion eventually is restricted by the planar target geometry. Spot size dependence can be investigated in the present invention by using a beam conditioner 24 and a lens 26 to create a laser focal spot 34 as shown in FIG. 4. Laser focal spot 34 can be elongated to overfill the narrow sample dimension, width W. Focal spot 34 has an $1/e^2$ intensity contour.

Similar results are shown for a painted sample of aluminum. The peak absorption coefficient occurs at very low incident energies. This is consistent with the observation that the painted samples are damaged severely at relatively low energies. No significant change in slope occurs at the flash threshold, since absorption already is near total. The decreased coupling above threshold is attributed to plasma shielding as described above, except that the painted surface produces a rapidly expanded plasma at lower energies.

The theoretical description of the method is based on the fact that the total energy absorbed in given by volume integral of the temperature rise $\Delta T$ in the sample. It does not depend upon the details of the temperature distribution. In a sample of length L and constant cross-sectional area A, the absorbed energy E depends only on the irradiation time, t, according to $$E(t) = \rho C A \int_0^{L(t)} \Delta T(z,t) dz \quad (1)$$

In equation one (1), z represents position along the length of the sample as mentioned previously. Equation 1 presumes that the sample area, A, specific heat, C, and mass density, $\rho$, are constant, and that thermal losses to radiation and convection are negligible.

After irradiation, the sample length L becomes a variable dependent on the irradiation time t such that $$L(t) = L_o + \frac{F(t) L(t)}{YA} + r \int_0^{L(t)} \Delta T(z,t) dz \quad (2)$$

$L_o$ is the unstretched length. The remaining terms represent sample elongation due to tensile load, F(t), and to thermal expansion. Young's modulus Y and the thermal expansion coefficient r are presumed constant. Before irradiation t=0, elongation is determined only by the applied tensile load, F(0). Thus, the original length at time 0 is $$L(0) = L_o + \frac{F(0) L(0)}{YA} \quad (3)$$

Subtraction of equation 3 from equation 2 yields the net elongation $\Delta L(t)$ due to irradiation. This elongation is taken up by the load cell which has elastic compliance $$\gamma_L = -\Delta L(t)/\Delta F(t). \quad (4)$$

The tensile relaxation $\Delta F(t)$ must satisfy $$-\gamma_L \Delta F(t) = \quad (5)$$

$$\frac{\Delta F(t) L(0)}{YA} \left[ 1 - \frac{F(t)\gamma}{L(0)} L \right] + r \int_0^{L(t)} T(z,t) dz.$$

The term in brackets is negligibly small if the experimental parameter F, L, and $\gamma_L$ are chosen carefully. Equations 5 and 1 together yield the desired expression for total optical energy absorbed as a function of the observed peak tensile relaxation. The gives the absorbed energy at time t as $$E(t) = -\frac{\rho C A}{r} (\gamma_L + \gamma_s) \Delta F(t) \quad (6)$$

where $\gamma_S$ is $$\gamma_s = \frac{L(0)}{YA} \quad (7)$$

The coupling coefficient $\alpha$ is obtained by dividing equation 6 by the incident energy $E_o$ yielding $$\alpha = -\frac{1}{E_o} \frac{\rho C A}{r} (\gamma_L + \gamma_s) \Delta F(t). \quad (8)$$

Figure 5:
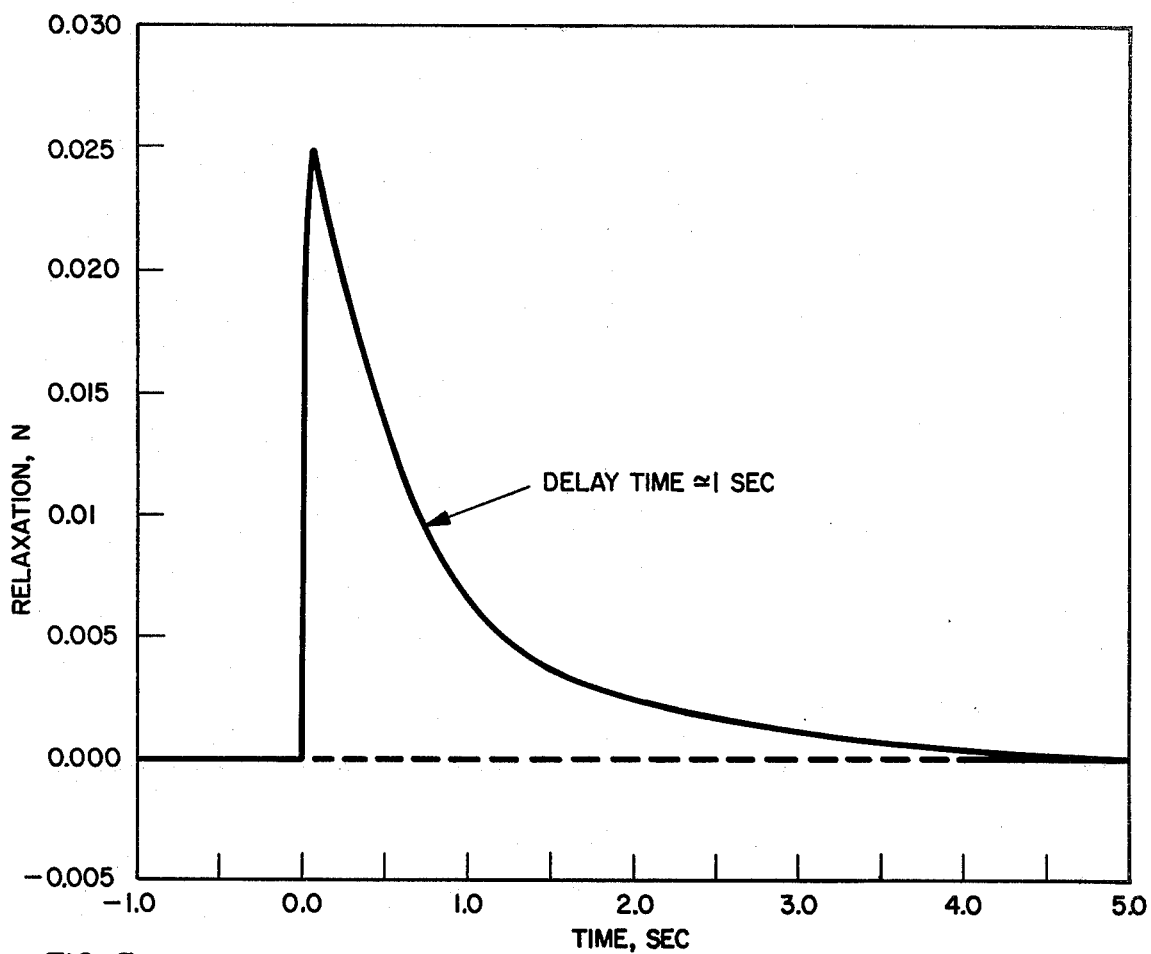
FIG. 5 shows a laser-induced tensile pulse.
Figure 6:
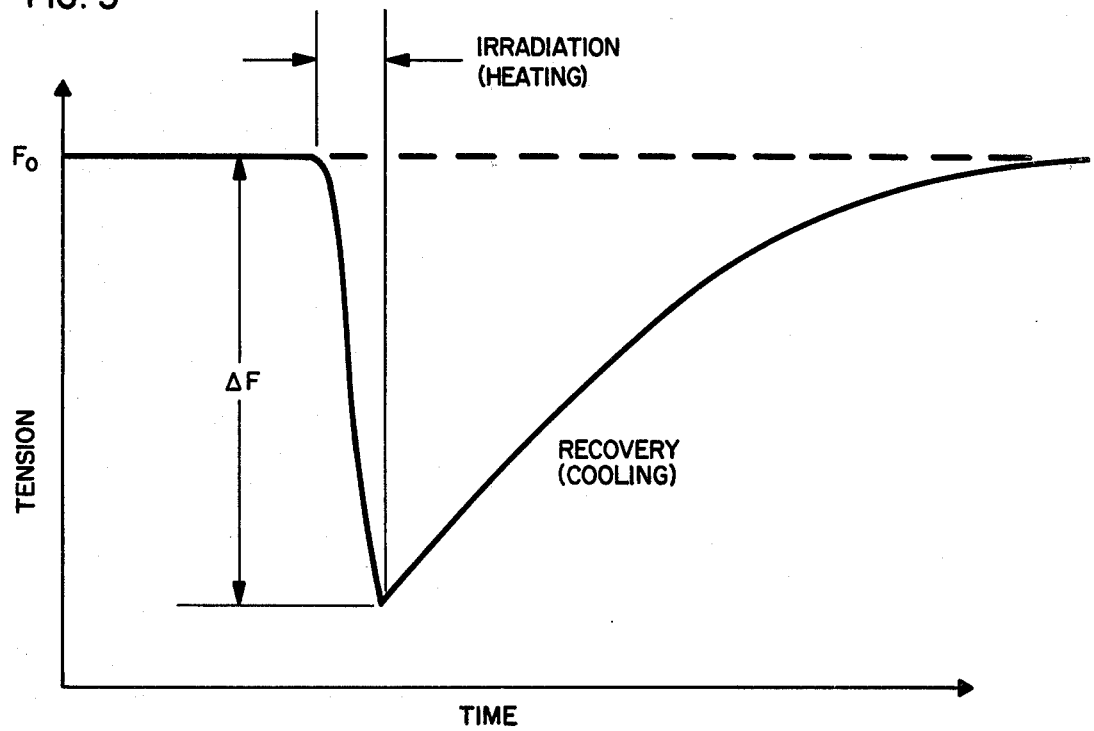
FIG. 6 shows the corresponding tensile relaxation that accompanies FIG. 5.

FIG. 5 shows a sample laser-induced tensile pulse. The total energy absorbed occurs very rapidly, followed by an exponential decay. FIG. 6 shows the corresponding tension relaxation of $\Delta F$ for such energy absorption.

It is obvious to those skilled in the art that numerous modifications and variations of the above invention can be made.

What is claimed is:

1. An apparatus for measuring the optical coupling coefficient of a sample comprising:
means for tensioning said sample a predetermined amount;
means for measuring said sample tension;
a light source for emitting a known amount of light incident on said sample; and
means for recording the change in said measuring means when said light is incident on said sample such that said optical coupling coefficient can be calculated from said recorded values.

2. An apparatus for measuring the optical coupling coefficient of a sample as described in claim 1 further comprising:
a beamsplitter placed in the path of light from said source for dividing said emitted light into two beams of known intensities relative to each other; and
means for detecting the absolute intensity of one of said beams placed in the path of the beam not incident on said sample.

3. An apparatus for measuring the optical coupling coefficient of a sample as described in claim 2 further comprising:
a beam conditioner in the path of said divided beam incident on said sample for matching the spatial distribution of said incident beam to the geometry of said sample; and
a lens for focusing said matched spatial distribution onto said sample.

4. An apparatus for measuring the optical coupling coefficient of a sample as described in any of claims 1, 2 or 3 where said light source comprises a pulsed laser with predetermined pulse repetition frequency.

5. A method of measuring the optical coupling coefficient of a sample comprising the steps of:
tensioning said sample a predetermined amount;
illuminating said sample with light of known intensity for a predetermined length of time;
measuring the tension on said sample before, during, and after illumination by said light;
recording the change in tension on said sample due to said light illumination; and
calculating the optical coupling coefficient of said sample according to the equation $$\alpha = -\frac{1}{E_o} \frac{\rho C A}{\Gamma} (\gamma_L + \gamma_s)\Delta F(t).$$

where:
$\alpha$ = optical coupling coefficient;
$E_o$ = incident energy;
$\rho$ = mass density of sample;
$C$ = specific heat of sample;
$A$ = sample area;
$\Delta F(t)$ = tensile relaxation;
$r$ = thermal expansion coefficient;
$\gamma_L$ = elastic compliance;
$L_o$ = unstretched length of sample; and
$Y$ = Young's modulus.

6. A method of measuring the optical coupling coefficient of a sample as described in claim 5 where said illumination step comprises illuminating the sample with a pulsed laser of predetermined pulse repetition frequency.

7. A method of measuring the optical coupling coefficient of a sample as described in claim 5 further comprising the steps of:
splitting said illumination light prior to its illuminating said sample into two light beams of known intensities relative to each other, only one of said beams used to illuminate said sample; and
detecting the absolute intensity of said beam not illuminating said sample.

8. A method of measuring the optical coupling coefficient of a sample as described in any of claims 5, 6, or 7 further comprising the steps of:
conditioning said beam illuminating said sample so said illuminating beam spatial distribution matches the geometric shape of said sample; and
focusing said conditioned illuminating beam onto said sample.

* * * * *